(12) United States Patent
Albert et al.

(10) Patent No.: US 12,097,035 B2
(45) Date of Patent: Sep. 24, 2024

(54) SYSTEMS AND METHODS OF QT INTERVAL ANALYSIS

(71) Applicant: AliveCor, Inc.

(72) Inventors: David E. Albert, Oklahoma City, OK (US); Alexander Vainius Valys, Sunnyvale, CA (US); Conner Daniel Cross Galloway, Sunnyvale, CA (US)

(73) Assignee: ALIVECOR, INC., Mountain View, CA (US)

( * ) Notice: Subject to any disclaimer, the term of this patent is extended or adjusted under 35 U.S.C. 154(b) by 702 days.

(21) Appl. No.: 17/054,130

(22) PCT Filed: May 8, 2019

(86) PCT No.: PCT/US2019/031322
§ 371 (c)(1),
(2) Date: Nov. 9, 2020

(87) PCT Pub. No.: WO2019/217556
PCT Pub. Date: Nov. 14, 2019

(65) Prior Publication Data
US 2021/0121117 A1    Apr. 29, 2021

Related U.S. Application Data

(60) Provisional application No. 62/668,691, filed on May 8, 2018.

(51) Int. Cl.
*A61B 5/36* (2021.01)
*A61B 5/00* (2006.01)
*A61B 5/28* (2021.01)
*A61B 5/353* (2021.01)
*G06N 3/08* (2023.01)
(Continued)

(52) U.S. Cl.
CPC .............. *A61B 5/36* (2021.01); *A61B 5/28* (2021.01); *A61B 5/353* (2021.01); *A61B 5/7267* (2013.01); *G06N 3/08* (2013.01); *G16H 30/20* (2018.01); *G16H 50/20* (2018.01)

(58) Field of Classification Search
CPC ....................................................... A61B 1/36
See application file for complete search history.

(56) References Cited

U.S. PATENT DOCUMENTS

2008/0262366 A1\* 10/2008 Hunt ............... A61B 5/349
600/516
2010/0056939 A1    3/2010 Tarassenko et al.
(Continued)

FOREIGN PATENT DOCUMENTS

WO     2017072250 A1    5/2017
WO     WO-2018045147 A1 \*  3/2018 ............. A61B 5/316

OTHER PUBLICATIONS

International Search Report and Written Opinion for International Application No. PCT/US2019/031322.

*Primary Examiner* — Brian T Gedeon
(74) *Attorney, Agent, or Firm* — WOMBLE BOND DICKINSON (US) LLP (57) ABSTRACT

Disclosed systems and method receive electrocardiogram (EKG) data of a subject. The EKG data comprises a record of at least a full beat of the subject. The EKG data is input into a machine learning model to generate an output. The output can include a segmentation of the full beat or a measurement of a QT interval of the subject.

17 Claims, 7 Drawing Sheets

(51) Int. Cl.
*G16H 30/20* (2018.01)
*G16H 50/20* (2018.01)

(56) References Cited

U.S. PATENT DOCUMENTS

| | | |
|---|---|---|
| 2011/0177503 A1 | 7/2011 | Spooner et al. |
| 2016/0135708 A1* | 5/2016 | Chakravarthy ...... A61B 5/7275 600/515 |
| 2017/0112401 A1* | 4/2017 | Rapin .................. A61B 5/7203 |
| 2018/0032689 A1 | 2/2018 | Kiranyaz et al. |

* cited by examiner

SYSTEMS AND METHODS OF QT INTERVAL ANALYSIS

RELATED APPLICATIONS

This application is a National Phase of International Application No. PCT/US2019/031322 filed 8 May 2019, which claims the benefit under 35 U.S.C. § 119(e) of U.S. Provisional Application No. 62/668,691 filed 8 May 2018, the entire contents of which are hereby incorporated by reference herein.

TECHNICAL FIELD

The disclosed embodiments relate generally to analysis of electrocardiogram (EKG) data.

BACKGROUND

One measured interval of a subject's EKG is known as the QT interval. The QT interval measures the time from the start of the Q-wave and the end of the T-wave. The start of the Q-wave is associated with the depolarization of the ventricles, while the T-wave is associated with the repolarization of the ventricles. The QT interval may vary by age, weight, race, health status, and other factors, but is generally expected to be within a certain range. In addition, the length of a QT interval may vary by heart rate. Accordingly, to normalize results, corrected QT (QTc) intervals may be used to standardize QT intervals at different heart rates. QT (or QTc) intervals over a threshold value are referred to as long-QT. A subject with a long-QT is referred to as having long-QT syndrome. Long-QT syndrome is associated with heart arrhythmias that can cause fainting, cardiac arrest, or sudden death.

Long QT syndrome can be inherited genetically in some subjects. Genetically acquired long QT syndrome may be referred to as congenital long QT. While some of those subjects may not exhibit a long QT in all EKGs, they are still at higher risk for arrhythmias and other complications. Long QT can also be the result of environmental factors. Long QT resulting from environmental factors may be referred to as acquired long QT. In particular, certain medications can lengthen the QT interval in certain subjects. Those having inherited long QT syndrome, as well as those with other conditions that are associated with QT prolongation, may be at additional risk when taking such medicines. Such conditions associated with QT prolongation can include female sex, bradycardia, hypokalemia, hypomagnesemia, hypocalcemia, diuretic agent use, hypothermia, a history of heart disease, or other conditions. Accordingly, detection of and monitoring for long QT in individuals can be important when prescribing certain medications, changing exercise patterns, or changing other lifestyle patterns.

DETAILED DESCRIPTION

Described herein are devices and techniques for measuring the length of QT intervals in individuals and detecting and monitoring long QT in those individuals. In some embodiments, one or more machine learning models can be used to measure a QT interval length from an EKG signal. The machine learning model can be trained to segment an EKG signal into time points associated with a Q-wave onset and a T-wave end from which a time difference can be calculated, or the QT length can be output directly by the machine learning model.

Long QT Syndrome is both a congenital and acquired disorder. The inherited form leaves 160,000 people in the U.S. vulnerable, and causes 3,000 to 4,000 sudden deaths in children and young adults annually. The acquired form of LQTS can be caused by nearly 100 FDA-approved medications, such as antibiotics and antidepressants. As many as 50% of patients with genetically confirmed LQTS have a normal QT interval on the standard ECG, so identifying these patients, who are at increased risk of arrhythmias and sudden cardiac death especially when exposed to medications with known QT prolonging potential, is crucial for correct diagnosis and treatment.

In a clinical setting, typically the length of a QT interval is measured using a 12 lead EKG. The 12 lead EKG provides multiple measurements of electric potential across different planes of the heart to provide different assessments of the heart's electrical activity. As such, different leads may provide clearer or more defined segments of a subject's EKG compared to other leads. For example, one lead of a 12 lead EKG may not clearly show a T-wave, while another lead of a 12 lead EKG may show a clear T-wave. Accordingly, practitioners traditionally use a 12 lead EKG to determine a QT interval. In some embodiments described herein, a QT measurement system inputs a single lead EKG into a machine learning model to determine a length of the QT interval. For example a lead I measurement may be used to determine an accurate QT measurement. In some embodiments, both a lead I and lead II measurement can be used as inputs to a machine learning model to measure the length of a QT interval. It should be understood, however, that any recording length as well as any other lead or combination of leads selected from leads I, II, III, aVR, aVL, aVF, V1, V2, V3, V4, V5, and V6 or any other lead configurations are suitable for use as inputs to the machine learning models as described herein.

Training a machine learning model may include using a training set of EKGs from a number of subjects. The training set of EKGs can include EKG signals of each subject and associated labels for those EKGs. For example, the EKGs may be labeled with a length of a QT interval or QTc. The EKGs may also be labeled with the timing of certain segments of the EKG. For example, the segmentation can include labels of the times of the beginning, middle, or end of PQRST waves in the training set. The machine learning model can then be trained on the example training data and associated labels.

While training, the machine learning model can be run with a number of techniques, as further discussed below. Generally, the training-EKG data will be input with labeled QT data. Depending on the type of machine learning model, the training EKG data may then be processed by a set of mathematical operations (e.g. addition, multiplication, convolution) involving weight matrices in a number of layers of the machine learning model. After processing, the machine learning model may then generate an output or prediction. The output or prediction is compared to the label (e.g., labeled QT interval) for the training data, the machine learning model may be updated, e.g., weight matrices may be updated using back propagation, so that the final output of the model better approximates the correct label, or known data, during a next processing stage. The process is continued with additional training data or repeated with the same training data until the model converges.

In some embodiments, the EKG data associated with subjects in the training data may be read by an EKG sensor as a number of samples. These samples may be digitized for input to the machine learning model during both training and application. For example, the EKG may represent data read in over a period of time. In some embodiments, the EKG may operate at approximately 300 hertz, 600 hertz, 1000 hertz, or at another frequency of sampling to provide accurate data for the EKG. The ERG data may be read into the machine learning model in periods of time. For example, an EKG signal of 10 seconds length may be used as the input EKG data. In some embodiments, rather than a continuous string of data, an average heartbeat may be determined by detecting each heartbeat present in the EKG signal, aligning each heartbeat based on a common feature such as the R-wave, and averaging each beat to produce an average amplitude at different parts of the beat. This may reduce noise or signal artifact present in the EKG recording.

The process of training the machine learning model may be repeated for each EKG in the training data. For example, the training may be performed by inputting each EKG with a labeled QT data into the machine learning model. The model may then be updated based on the difference between output prediction of the machine learning model and the correct output (label), e.g., weight matrices are updated. The process may be repeated through all the EKG data multiple times until the outputs of the machine learning model are within a threshold of accuracy. For example, the threshold may be set to be within a set threshold of QT interval values for each EKG. The threshold may also be set such that it is within a threshold of a measured value at least for a threshold number of EKGs.

While various machine learning models may be used, in some embodiments a convolutional neural net, a recurrent neural net, or a combination of a convolutional neural net and a recurrent neural net may be used. For example, a machine learning model may include 4 convolutional layer and 2 fully connected layers. In some embodiments, fewer or additional layers of different types may also be used. Furthermore, in some embodiments, drop out regularization, skip connections, max pooling, or other techniques may be used.

In an example, a neural network for determining QT intervals contains three convolutional layers prior to a three-layer recurrent neural network with LSTM cells. The first convolutional layer operates on a 450-sample average beat with an arbitrary number of leads. The layer contains 16 filters with a stride of 2. The second convolutional layer also contains 16 filters with a stride of 2. The third convolutional layer also contains 16 filters with a stride of 2. All three layers use relu-activation functions and employ batch normalization. There is a dropout layer between the second and third convolutional layers. The action of the three convolutional layers effectively down-samples the 450-sample average beat by a factor of 8. The input into the LSTM cells is thus 56 samples of a vector with 16 features. The three LSTM cells each have 256 units, 0 are simply stacked, and contain dropout layers between the cells. The output of the third LSTM cell after the cells process the 56 samples output from the convolutional layer is passed through a linear fully connected layer whose output has dimension 1, namely the estimated QT value for the average beat. In some embodiments, other machine learning models can include fewer or additional layers, different dropout, max pooling, normalization, or other feature implementation, different numbers and sizes of filters, or changes to other parameters of the machine learning models.

After training, a subject's EKG data may be input into the machine learning model that will determine a length of the subject's QT interval. In some embodiments, the EKG may be applied as an input to the machine learning model in the same or similar manner as during training. For example, if ten second periods of EKG data were used to train a machine learning system, the same type of EKG data may be input to the machine learning model to determine a length of the QT interval. Similarly, if an average heartbeat over a certain period of time was used for the training data, the same average heartbeat pre-processing may be applied to the data input into the trained machine learning model. In some embodiments, the training data may include hundreds, thousands, tens of thousands, millions, or other quantity of EKG data and associated QT interval data used to label the EKG data.

In some embodiments, training of a machine learning model may be performed at a computer or server capable of large amounts of data processing. For example, a computing or server system may be used to train a machine learning model based on labeled EKG data. In some embodiments, after training, a machine learning model may be stored on and applied by a different computer system than that used for training. For example, a computing system or server system may be used to train a machine learning model, however, after training, the machine learning model may be transferred to and used by an individual's personal computer, mobile device, smart phone, wearable computing device (e.g., smart watch or health band), or the like, where input data is supplied to the trained model via the personal computer, smart watch or wearable computing device. Of course, in some implementations, different servers, computer systems, personal computers, mobile devices, or the like may be used to perform any tasks as described herein, e.g, a distributed network.

Figure 7:
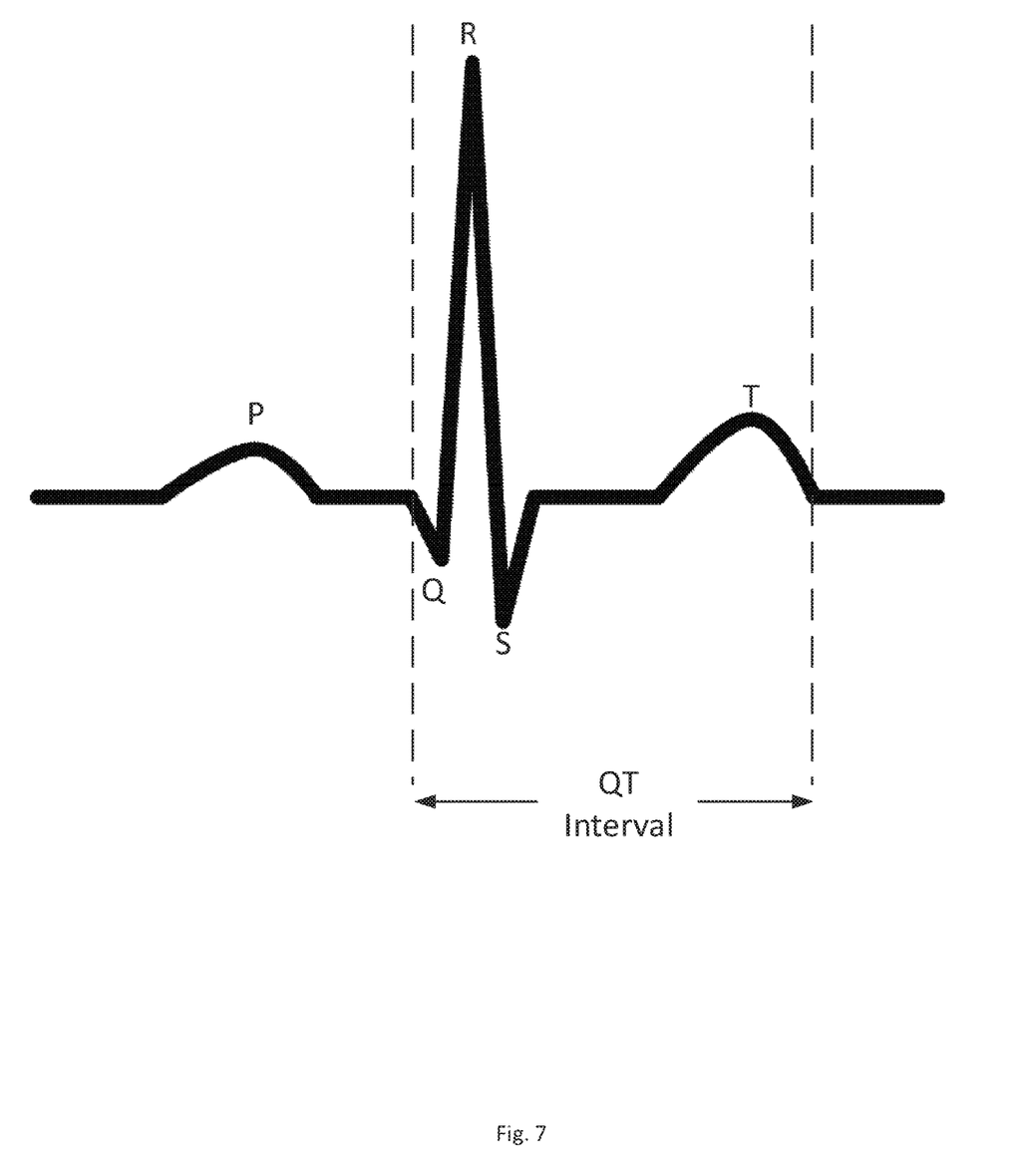
FIG. 7 illustrates example EKG signals, according to aspects of the disclosure.

For reference, FIG. 7 shows a general EKG having standard features. For example, the EKG shows two measured beats. Each beat has a P-wave, a QRS complex, and a T-wave. Each segment has different amplitudes and slopes at various points. As shown, the QT interval is the length of time from the beginning of the Q-wave and the end of the T-wave. Although the elements of these features may be built in to the machine learning model, they are not necessarily individually analyzed by the model. For example, the machine learning model may learn features or relations between features during training that are different than those shown. Furthermore, as discussed above, certain individual's may have different features than shown in a typical EKG. For example, some individuals may not have a well-defined T-wave as shown, but may instead have a bi-phasic T-wave, an inverted T-wave, or other unusual features. Accordingly, although described as learning features to measure the QT interval of an individual, a machine learning model may be using other features than as shown in FIG. 7 or than those traditionally used by healthcare professionals.

The systems and techniques as described herein are generally discussed in the context of the QT interval, the period between the QRS onset and T-wave end. In addition to the QT interval, the same techniques may be applied to other quantitative measures of ECG features. For example, the systems and methods disclosed herein may also be applied to measure a J-T peak interval (the interval between the J-point and the peak of the T-wave), a T-peak-T-end interval (the interval between the peak of the T-wave and the end of the T-wave), or other measures of the T-wave morphology, including but not limited to T-wave amplitude, T-wave shape, T-wave upslope, T-wave downslope, T-wave concavity, T-wave area, and combinations of these features. These other measures may respond to different physiological influences than the QT interval. These measures may be used instead of or in combination with the QT interval. Multiple measures can be used and evaluated in the same system.

Figure 1:
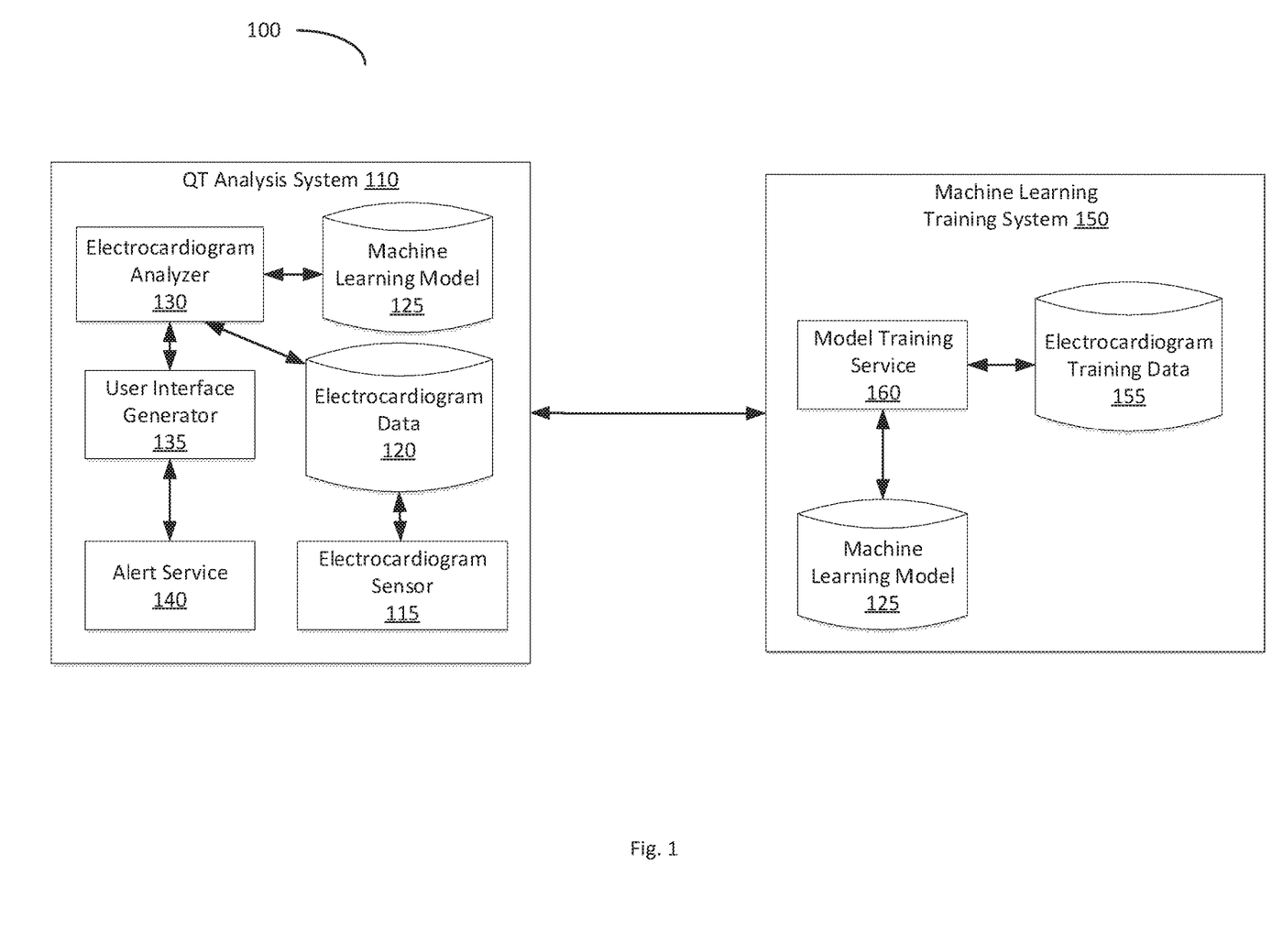
FIG. 1 illustrates an example system to provide QT interval measurement as discussed herein, according to aspects of the disclosure.

FIG. 1 illustrates an example QT interval measurement system 100 that supports the measurement and analysis of QT intervals as described herein. The QT interval measurement system 100 may include QT analysis system 110 and a machine learning training system 150. Although shown as separate components, in some embodiments, the QT analysis system 100 and the machine learning training system 150 may be part of the same computer system. In some embodiments, the QT analysis system 110 and the machine learning training system 150 may be remote components connected over a network. For example, the QT analysis system 110 may be located on a personal device such as a mobile device, personal computer, smart watch or wearable fitness band (collectively "wearable computing device"), or the like. The machine learning training system may be located on the same device as the QT analysis system 110 or on a remote device such as a central server.

In some embodiments, there may be fewer or additional components than shown in FIG. 1. For example, in some embodiments there may be additional QT analysis systems 110. Accordingly, additional QT analysis systems 110 may be used for providing QT interval measurement for a number of different subjects. For example, a machine learning model 125 may be provided to a number of QT analysis systems 110 at different computing devices to provide predictions of QT measurements at different locations and for different subjects. Furthermore, while an EKG sensor 115 is shown as part of QT analysis system 100, in some embodiments, there may be different EKG sensors (not shown) that are used in different parts of training and application stages of a machine learning model.

The machine learning training system 150 may include model training service 160, labeled EKG training data 155, and machine learning model 125. The EKG training data 155 includes labeled EKGs taken from a number of subjects in a population. The EKGs may include a period of an EKG signal for each subject, e.g., a representation of 10 seconds, 30 seconds, 5 seconds, or another length of time of an EKG. In some embodiments, the EKGs include a single beat of each subject's EKG. EKG training data 155 also includes one or more labels associated with each EKG stored in the data. For example, labels can include identification of start or end times of one or more of PQRST waves. The labels can also include a length of a QT interval for a beat within the EKG data. For example, an EKG signal may have been labeled by an expert such as a cardiologist. In some embodiments, the EKG data may also be labeled with a classification of long QT or not long QT. In some embodiments, the EKG training data 155 may include additional data associated with individuals from which the EKG data was obtained. For example, the EKG training data 155 may include height, weight, sex, race, health conditions, or other data about subjects associated with an EKG. Any part of or all of the labeled EKG data can be included as an input to a model training service 160 to train the machine learning model 125 to learn to predict various aspects of EKGs input into the trained model, for example the QT-interval, QTc, QT-syndrome etc.

In some embodiments, multiple EKG waveforms are averaged to form a single averaged waveform that serves as the input for the model training service 160. For example, the EKG training data 155 may be pre-processed to form a set of inputs with labeled data for the model training service. Each of the inputs may be an averaged waveform of heartbeats located within an EKG signal. In some embodiments, the EKG data may be stored over a complete waveform of a single heartbeat. However, in some embodiments, additional pre-processing may be performed such as smoothing, noise reduction, or other processing.

In some embodiments, the EKG training data includes EKG data from a single lead. For example, the sample EKGs may include a lead I measurement of each subject. In some embodiments, the EKG training data can include EKG data from multiple leads. For example, the EKG data can include a lead I and lead II measurement for each subject. It should be understood, however, that any recording length as well as any other lead or combination of leads selected from leads I, II, III, aVR, aVL, aVF, V1, V2, V3, V4, V5, and V6 are suitable for use as inputs to model training service 160. In a further example, using a three-electrode mobile sensor, one can simultaneously obtain Leads I (left-right arm), II (right arm-left leg) and III (left arm-left leg), from which leads aVR, aVL and aVF can be mathematically derived giving 6 leads from which to determine the QT interval using a mobile EKG sensing device. The same leads (I, II, and III) could also be used in a non-mobile, hospital setting, or the mobile embodiment could be used the hospital setting too (e.g., waiting room).

The machine learning model 125 may start as an untrained or generic machine learning model. For example, the machine learning model 125 may start with randomized weight values for a number of matrices within the model. The machine learning model 125 may be set with a number of convolutional layers, recurrent layers, or the like prior to training by the model training service 160.

In some embodiments, the machine learning model 125 may be a recurrent neural network. A recurrent neural network may receive sequential data as an input, such as consecutive EKG samples or beats, and then the recurrent neural network updates its internal state at every time step. In some embodiments the machine learning model may be a convolutional neural network. A convolutional neural network may include a number of convolutional layers that apply convolution operations using weight matrices and non-linearities to identify one or more features in the input data. The output of each convolutional layer may then be passed to another layer to provide further analysis. In some embodiments, the machine learning model 125 may have a combination of recurrent and convolutional layers that identify and quantify different features in input data.

The model training service 160 may train a model based on each of the labeled EKGs in the EKG training data 155. In some embodiments, the model training service 160 uses automatic statistical analysis of labeled data in order to determine which features to extract and/or analyze from a sensed EKG. The model training service 160 may extract features from an EKG based on labeled EKG training data 155 that it receives.

In some embodiments, the model training service 160 may be configured to receive a raw EKG data as an input. For example, an input to the model training service 160 may be 10 seconds or more of an EKG signal from lead I of an EKG sensor 115. The model training service 160 uses the untrained machine learning model 125 as a function approximator, mapping a high dimensional input (the raw EKG waveform) into an output value for the data (e.g. a QT interval measurement). The machine learning model may provide direct approximation of the length of a QT interval, a classification of the subject as having long QT syndrome or not having long QT syndrome, or other outputs. Based on differences between the output of the machine learning model and the labelled data, the model training service 160 may update the machine learning model to better fit the labeled data.

The model training service 160 may provide each EKG in EKG training data 155 to the machine learning model 125 until the machine learning model 125 predicts the labels with sufficient accuracy. For example, the model training service 160 may determine that the machine learning model 125 has converged or is trained if it can predict the labels in the EKG training data 155 to within a threshold difference of the known value. In some embodiments, only part of the EKG training data 155 may be provided to the model training service 160 to train the machine learning model 125 and the remaining EKG training data 155 may be stored as a verification set. The model training service 160 may then validate the machine learning model 125 by testing the model on the verification set.

In some embodiments, the machine learning model 125 can be trained to provide an output of a QT interval length based on the training. Thus, each EKG signal in the EKG training data is labeled with a QT interval length. For example, the label can be provided by an expert such as a cardiologist, by a numerical analysis of EKG data, or based on other data. In some embodiments, the labels for the EKG training data may have been determined or generated from a 12 lead EKG system, but the EKG training data may only include a subset of the leads, such as lead I, lead II, or lead I and lead II with the labels determined or generated from up to 12 leads. During training, the model training service 160 can input each of the EKG signals into the machine learning model 125 and compare the output estimated QT interval to the known label. Depending on the differences between the two values, the model training service 160 updates the weighting of various variables in a neural network. For example, if the estimated QT interval is exactly the same as the label (or within a threshold) then the model training service160 may not update the neural network. If the estimated QT interval is higher or lower than the label, then the model training service 160 may update weights in one or more layers of the neural network accordingly. The model training service 160 repeats the process for each EKG signal in the EKG training data 155 until the machine learning model 125 converges. For example, in some embodiments, the machine learning model 125 may be considered to have converged when it can accurately generate an output within 20 ms of the label for at least a threshold percentage of the EKG training data 155 or a set of verification data. In various embodiments, other thresholds may be used by the model training service 160, or it may repeat for a predefined amount of time or number of cycles.

In some embodiments, the machine learning model 125 can be trained to segment a waveform representing an individual beat in EKG data. Thus, each ERG signal in the EKG training data is labeled with one or more time values indicating an event within the EKG. Events can include the start, end, or midpoint of one or more of the PQRS or T-waves. For the purposes of determining QT interval length in this embodiment, the data is labeled at least with a time indicating the beginning of the Q-wave and the end of the T-wave. However, other points such as peak of the R-wave, start of the P-wave, or the like may also be labeled. The time labels can be provided by an expert such as a cardiologist, by a numerical analysis of EKG data, or based on other data. In some embodiments, the labels for the EKG training data may have been determined or generated using a 12 lead EKG system, but the EKG training data may only include a subset of the leads, such as lead I, lead II, or lead I and lead II, or any combination of the 12 leads. During training the model, training service 160 can input each of the EKG signal into the machine learning model 125 and compare the output estimated times to the respective known labeled times. For example, an estimated start of the Q-wave is compared to a labeled start of the Q-wave and an estimated end of the T-wave is compared to a labeled end of the T-wave. Depending on the differences between estimated and known labeled data, the model training service 160 updates the weighting of various variables in a neural network. The model training service 160 repeats the process for each EKG signal in the EKG training data 155 until the machine learning model 125 converges and is able to generate accurate times for labeled events within an EKG signal. For example, in some embodiments, the machine learning model 125 may be considered to have converged when it can generate an output within 20 ms of the label for at least a threshold percentage of the EKG training data 155 or a set of verification data. In various embodiments, other thresholds may be used by the model training service 160, or it may repeat for a predefined amount of time or number of cycles.

In some embodiments, the machine learning model 125 can be trained to provide an output classification of whether a subject has long QT syndrome. In some embodiments, the classification may be whether a currently analyzed EKG estimates or predicts a QT interval over a threshold length. In other embodiments, the classification may be whether the currently analyzed EKG belongs to a person with a genetic mutation that causes long QT syndrome. Furthermore, in some embodiments, the classification can be between different genetic mutations causing long QT syndrome. Thus, a particular genetic mutation may be one classification and a second genetic mutation may be another classification. Thus, each EKG signal in the EKG training data may be labeled as having long QT syndrome or not (or other more specific labels). During training, the model training service 160 can input each of the EKG signals into the machine learning model 125 and compare the output classifications to the labeled classifications. The model training service 160 can update one or more layers of a neural network based on the difference between the output classifications and labeled classification. The model training service 160 repeats the process for each EKG signal in the EKG training data 155 until the machine learning model 125 converges and is able to accurately classify EKGs. For example, in some embodiments, the machine learning model 125 may be considered to have converged when it can accurately classify a threshold percentage of the EKG training data 155 or a verification set of data. In various embodiments, other thresholds may be used by the model training service 160, or it may repeat for a predefined amount of time or number of cycles.

After a machine learning model 125 has been generated and verified, it can be provided to one or more QT analysis systems 110. For example, as the machine learning model 125 is trained on EKG training data 155 from across a population of individuals, it can be used on EKGs not stored in EKG training data 155 or used as training examples, which are input into machine learning model 125 to predict a length of a QT interval for a subject. In some embodiments, the input EKGs to learning model 125 may be used by machine learning training system 150 to retrain a machine learning model 125 to improve the model. As a new machine learning model 125 is generated, it may be pushed as an update to QT analysis system 110.

The QT analysis system 110 in FIG. 1 may provide data from an EKG sensor 115 to store as EKG data 120. In some embodiments, the EKG sensor 115 may be separate from the QT analysis system 110 and may provide an EKG signal remotely to the QT analysis system 110. The EKG data 120 may then be input to machine learning model 125 by EKG analyzer 130. The machine learning model 125 may be the same as was trained by machine learning system 150. In some embodiments, the machine learning model 125, the EKG analyzer 130, or other components of the QT analysis system 110 may be on a separate computing system than the QT analysis system 110. For example, the machine learning training system 150 may have one or more components of the QT analysis system 110.

The EKG analyzer 130 may apply the machine learning model 125 by inputting an EKG signal from EKG data 120 to EKG analyzer 130. As discussed herein, the ERG data may be pre-processed into set periods of time, average heartbeats, smoothed, noise reduced, or otherwise provided to the EKG analyzer 130. The EKG analyzer 130 may then input an EKG signal from EKG data 120 to the machine learning model 125 to generate an output of a QT interval length, an EKG segmentation, or a classification In the case that an EKG segmentation is provided, the EKG analyzer 130 can use the provided segmentations to calculate the QT interval. The EKG data 120 that is input to the machine learning model 125 may be provided in the same manner as that for the EKG training data 155 used to train the model. For example, if the EKG training data 155 was provided as ten second periods, the EKG analyzer 130 provides one or more ten second periods of EKG to the machine learning model 125.

In some embodiments, a user interface generator 135 provides the analyzed data to a user interface. For example, the user interface generator 135 may generate a user interface including one or more of a QT interval measurement, an EKG output, a QT interval classification, or a combination of outputs. For example, in some embodiments, a user interface generator 135 may provide a user interface as described with reference to FIG. 3.

In some embodiments, a QT analysis system 110 includes an alert service 140. The alert service 140 may generate an alert to an individual (e.g., a subject, relative, care giver, or health professional) if the machine learning model 125 provides a classification that a QT interval is over a threshold value. In some embodiments, the threshold value may be set at 500 ms, (150 ms, 400 ms, or another length of time representative of long QT intervals. A set threshold can be used for all subjects, or the threshold value may also be calculated based on an individual's age, height, weight, or other factors. The QT interval may also be converted to a QTc value based on the heart rate of the subject for comparison to a threshold. In some embodiments, a threshold level for a subject is generated based on prior measurements for the subject. For example, if a subject has been measured with a normal QT interval length, then on a subsequent measurement, the subject is measured with a longer QT interval length, that may indicate a need for further monitoring of the subject. Comparison to QT interval history for an individual may provide additional insight compared to a static measurement of a subject's QT interval. The threshold may also be updated based on other information about changes for a subject. Furthermore, the alert service 140 may provide additional alerts to other individuals. For example, an alert may be provided to a doctor, a caretaker, a health professional, a significant other, or the like. In addition, a record of the long QT may be added to medical records. Additionally, the QT analysis system 110 may recommend changing a dosage or to stop taking a medication.

Figure 2:
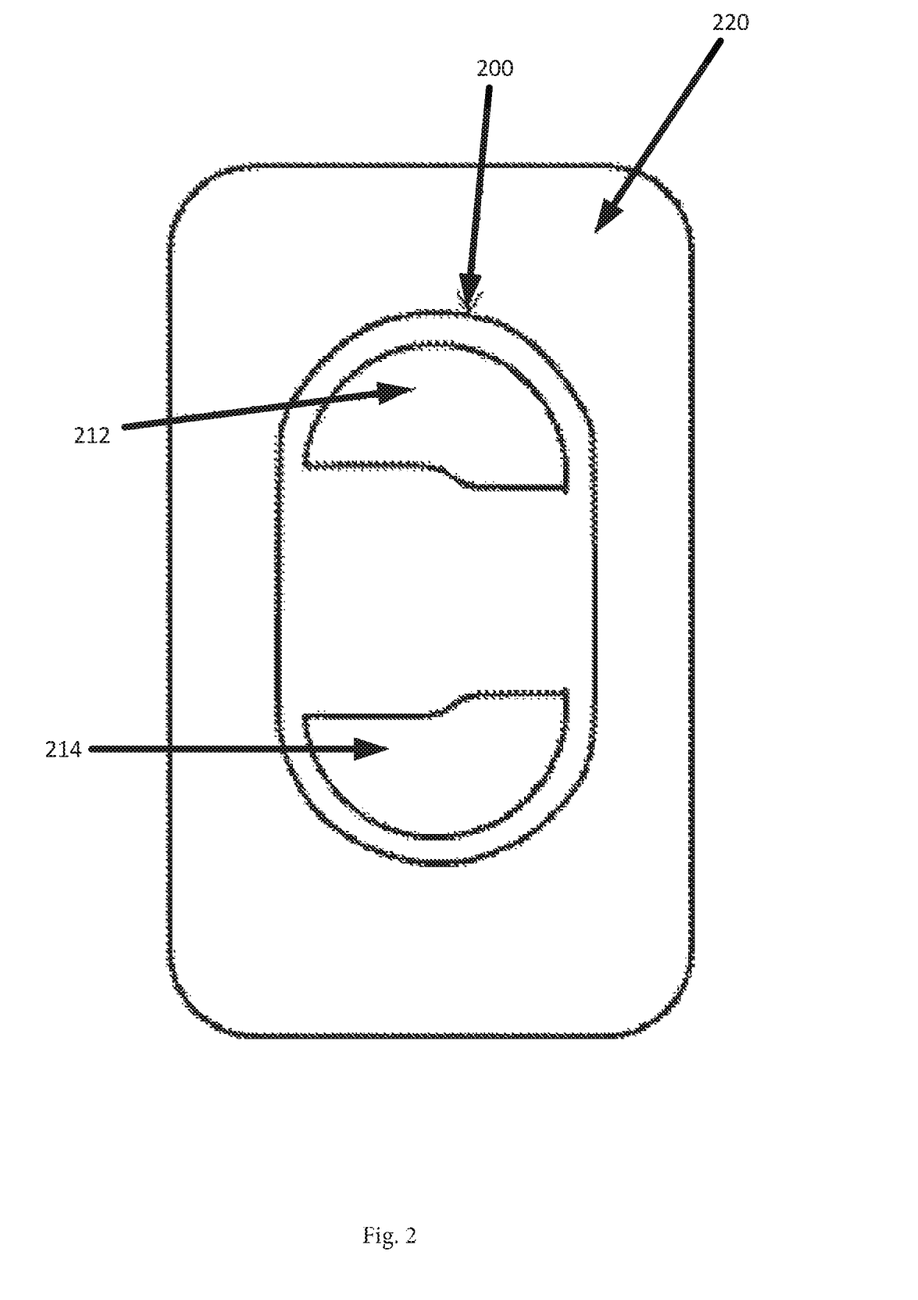
FIG. 2 illustrates an example electrocardiogram sensor, according to aspects of the disclosure.

FIG. 2 is an example EKG sensor 200 that can be used in accordance with some embodiments of the present disclosure. The EKG sensor 200 can be the same or similar to EKG sensor 112 as described with reference to FIG. 1. In FIG. 2, the EKG sensor 200 is shown coupled to a mobile computing device 220, however, in other embodiments, the EKG sensor 200 may be integrated into the mobile computing device 220. In various embodiments, the EKG sensor may also be coupled, in communication with, or integrated into a personal computer, mobile device, smart phone, wearable computing device (e.g., smart watch or health band), or the like. Sensor 200, as similarly described above, may have 3 electrodes for obtaining up to 6 leads (I, II, III, aVR, aVL, and aVF) remote from a medical center (e.g., hospital or doctor's office) using the mobile computing device 220.

The EKG sensor 200 includes a first sensor pad 212 and a second sensor pad 214. The sensor pads 212, 214 can be electrodes or enable electrical connection to electrodes. The EKG sensor 200 can measure the potential difference across the electrodes to record EKG data for a subject. In some embodiments, the EKG sensor 200 is designed for a subject to take a lead I EKG reading by having a subject place their left hand on one sensor pad 212, 214 and their right hand on the other sensor pad 212, 214. In some embodiments, the EKG sensor includes a processing device that performs QT interval analysis as described with reference to FIG. 1, The EKG data can also be provided to the mobile computing device 220 or another computing device to perform the QT interval analysis as described with reference to FIG. 1.

Figure 3:
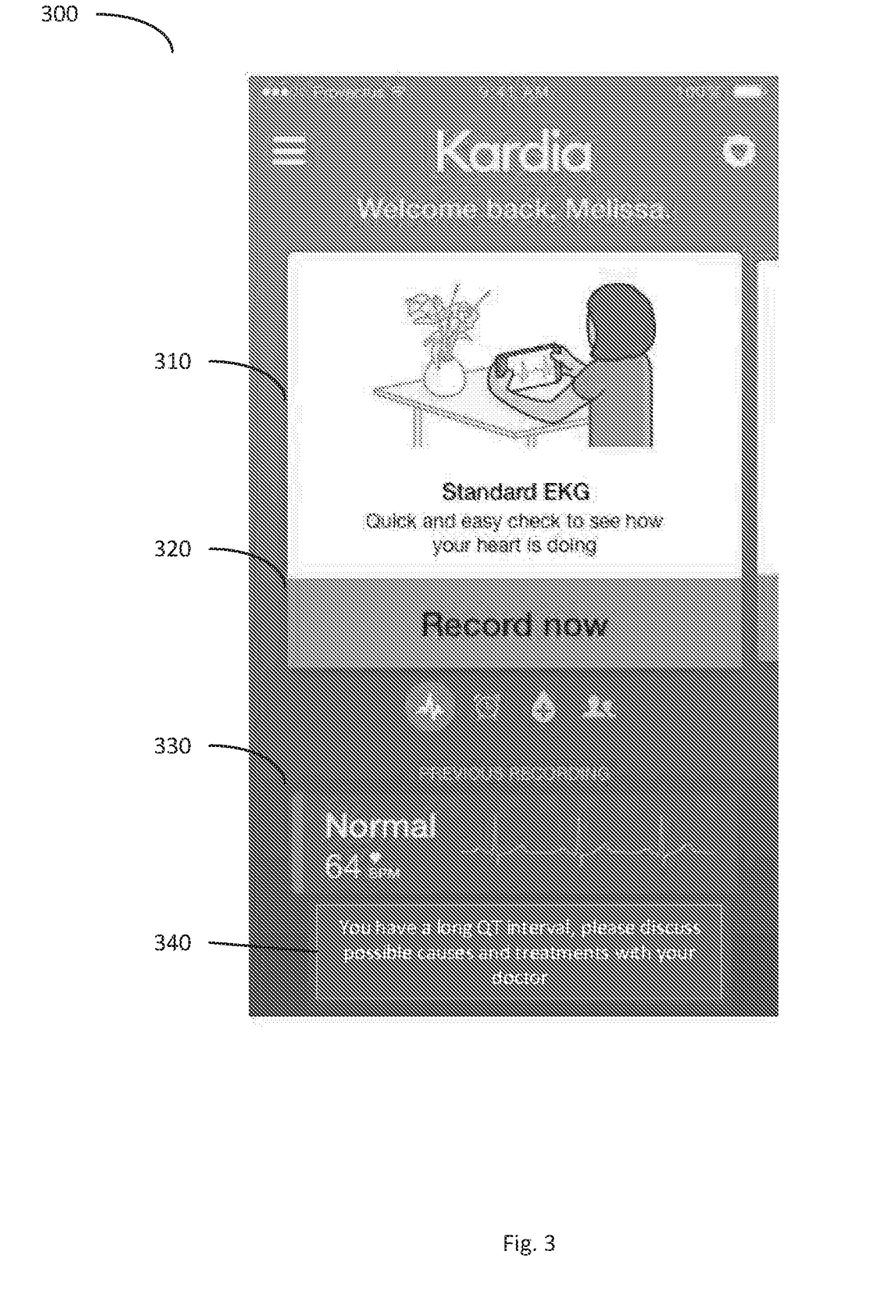
FIG. 3 illustrates an example user interface as generated by a QT interval measurement system as discussed herein, according to aspects of the disclosure.

FIG. 3 depicts an example user interface 300 showing a QT analysis system as described herein. For example, in some embodiments the user interface 300 may be generated by user interface generator 135 as described in FIG. 1. The user interface 300, or variants thereof, may be displayed on a mobile device, a personal computer, a web browser, a smart watch, or other computing devices.

The user interface 300 includes an interface 310 prompting a user to perform a standard EKG. The user may have an option 320 to record the EKG when an EKG sensor is in place. The EKG 330 may be displayed as it is recorded by the individual. As shown in FIG. 3, the user interface 300 provides an output 340 indicating that the subject has a long QT interval. This may be generated by the alert service 140 in response to an indication from the EKG analyzer 130 that the output of the machine learning model 125 indicates the long QT interval. In some embodiments, the user interface 300 may include the measurement of the QT interval of the subject. In some embodiments, if the QT interval is over a threshold, but typically the subject does not have a long QT, the QT analysis system may confirm the identity of the subject and/or prompt the subject to indicate whether she is taking any new medications or has made any other lifestyle changes. In this manner the system can help identify any potential issues that may arise from increased QT lengths resulting from medications or other factors. The capability to identify changes in QT intervals in an individual may prove very useful in drug studies, where it is important to understand the impacts investigative drugs have on QT intervals. This capability may also be useful in monitoring subjects while taking medications that may impact their QT intervals. Importantly, this monitoring (for studies or for normal subjects) can be done remotely and with fewer than 12 leads, and as few as 1, 2, 3, or 6 leads, making this aspect of the present invention highly useful for at least the purposes mentioned.

In some embodiments, a user interface generator may provide the length of the QT interval to the user regardless of the length. An alert service may use the data provided by the machine learning model to determine whether to alert the individual to additional issues with the user's QT interval. For example, even if the QT interval is below clinical levels of long-QT, the alert service can provide an indication to the subject that their QT interval is increasing and address potential issues before from an increased or increasing QT interval. As shown in user interface element 340, in some embodiments, a user interface may provide an alert and a recommendation to contact a doctor or physician. The alert may also be sent to others such as a medical professional family or loved ones. In some embodiments, an alert service may request a retest of an EKG prior to providing an alert that the subject has long QT syndrome.

Figure 4:
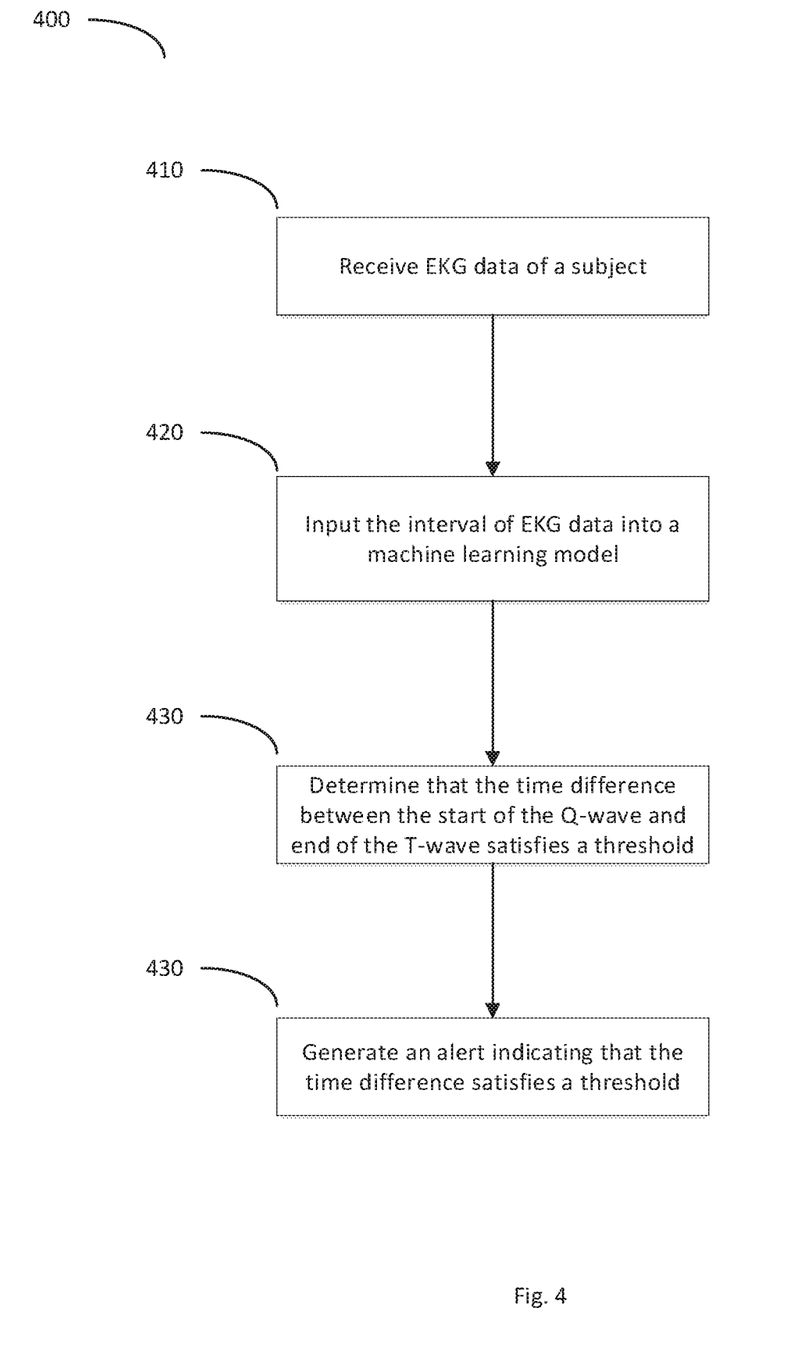
FIG. 4 illustrates flow diagram of processes as performed by a QT interval measurement system, according to aspects of the disclosure.

FIG. 4 depicts a data flow 400 illustrating the application of a machine learning model to an EKG of a subject. In some embodiments, the processes described with respect to FIG. 4 may be performed by one or more components of the QT interval measurement system 100 as described with reference to FIG. 1.

Beginning in block 410, a QT analysis system may receive EKG data from an EKG sensor. For example, the EKG sensor may provide real-time electric potential data of an individual's heartbeats. In some embodiments, the EKG sensor may be a 1, 2, 3 or 6 leads sensor and up to 12 leads. In some embodiments, the EKG data is received by a processing device coupled to the EKG sensor. The EKG data may additionally or alternatively be communicated to a remote device.

In block 420, the QT analysis system may apply a machine learning model to the EKG of the subject. In some embodiments, the machine learning model has been trained on EKG training samples of a population of subjects having known QT interval lengths. In some embodiments, the machine learning model may generate the QT interval of the subject straight from the input EKG. In some embodiments, the machine learning model generates a time associated with a Q-wave and a time associated with the T-wave and calculates the QT interval. In some embodiments, the output of the machine learning model may be a prediction of whether the subject has one or more genetic abnormalities associated with long QT syndrome, even if the EKG doesn't show a long QT interval.

In block 430, the QT analysis system determines that the time difference between the start of the Q-wave and the end of the T-wave satisfies a threshold for long QT or normal. The threshold may be set for an entire population. For example, the threshold may be set to 500 ms. In some embodiments, the threshold may be adjusted based on characteristics of the subject, such as age, gender, height, weight, or other factors. In some embodiments, the QT interval is adjusted to a QTc measurement prior to comparing to a threshold.

In block 440, the QT analysis system generates an alert indicating that the QT interval satisfies the threshold, e.g., the subject has a long QT interval. In some embodiments, the alert may be presented to the subject on a user interface of a mobile device or other computing device. In some embodiments, the alert may also be entered into a medical record of the subject or provided as an alert to a medical practitioner monitoring the subject, a family member or other pre-designated person who the user may want to notify.

Figure 5:
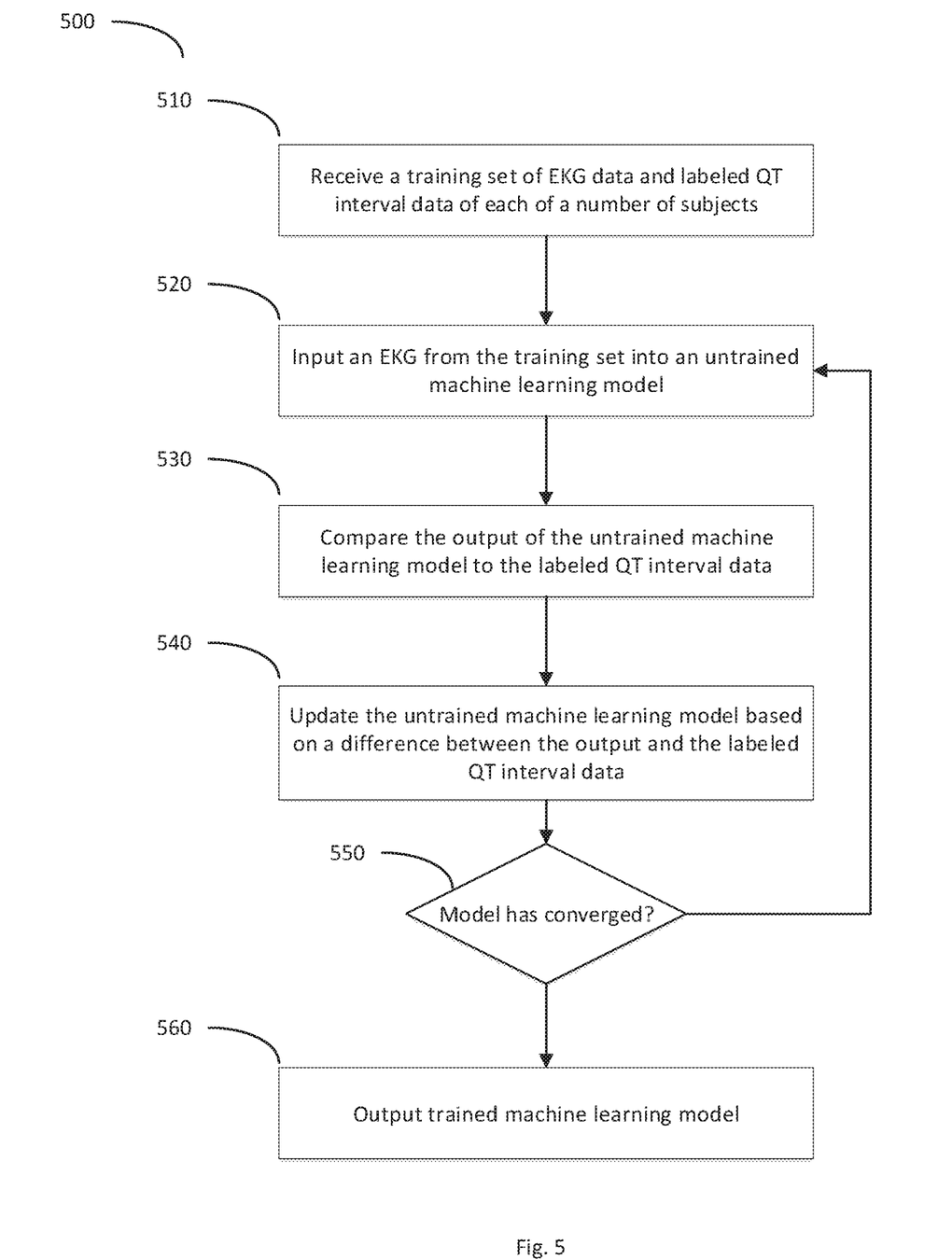
FIG. 5 illustrates flow diagram of processes as performed by a QT interval measurement system, according to aspects of the disclosure.

FIG. 5 depicts a data flow 500 illustrating training of a machine learning model using a training set of EKG data. In some embodiments, the processes described with respect to FIG. 5 may be performed by one or more components of the systems as described with reference to FIG. 1.

Beginning in block 510, a QT analysis system may receive EKG data and one or more QT interval labels of each of a number of subjects. For example, the data may be aggregated from patients in a doctor's office or hospital, from research subjects, or from other sources. In some embodiments, the training set of EKG data may include data from a 1 lead sensor or a 2 lead sensor. In various embodiments, the EKG data may also be from a 3 lead sensor, a 4 lead sensor, a 6 lead sensor, or a 12 lead sensor. As explained above, 2 or 3 electrode sensors have the ability to simultaneously collect 1, 2, 3 or 6 lead ECGs at a location remote from the professional healthcare location. The present invention may also be implemented with the conventional 12-lead ECG taken at a professional healthcare location, and any combination of those 12-leads may be used to train the machine learning models or as input into the trained machine learning models.

In block 520, the QT analysis system may input EKG data of a subject, along with labeled QT length data, into an untrained machine learning model as part of a process to train the model. For example, the EKG data for a subject may be provided to the untrained machine learning model. The untrained machine learning model then processes the EKG data to generate an output. The output may be an estimated QT interval, estimated times of Q-waves or T-waves, an estimated classifier of whether the subject has long QT-syndrome, or a combination of outputs. The estimations from the untrained machine learning model can then be compared to known values in the labels for the EKG data in order to train the machine learning model and improve the estimations.

In block 530, the QT analysis system compares the output of the untrained machine learning model to the labeled QT interval data. For example, the QT analysis system may determine that the estimate was too short or too long as compared to the known label. In some embodiments, the QT analysis system may compare multiple outputs of the untrained machine learning model to multiple known labels in the labeled QT interval data.

In block 540, the QT analysis system can update the machine learning model based on comparing the output of the machine learning training model and the label. For example, the QT analysis system may update the untrained machine learning model by updating weights of matrices in one or more layers of the machine learning model.

In block 550, the QT analysis system determines whether the model has converged. The QT analysis system can determine that the model has converged when it can provide an accurate output for at least a threshold amount of the training set of EKGs or a threshold amount of a verification set. In some embodiments, instead of determining that the model has converged, the QT analysis system can determine in block 550 that the untrained machine learning model has been trained through a set number of cycles, for a set amount of time, or another threshold.

In block 560, the QT analysis system outputs a trained machine learning model. After the machine learning model is trained, it may be used to test EKGs received from new subjects to measure QT intervals or predict whether a subject has long QT syndrome. In some embodiments, the trained machine learning model may be provided to or place onto computing devices associated with one or more new subjects to measure or predict their QT intervals or test for long QT syndrome.

Figure 6:
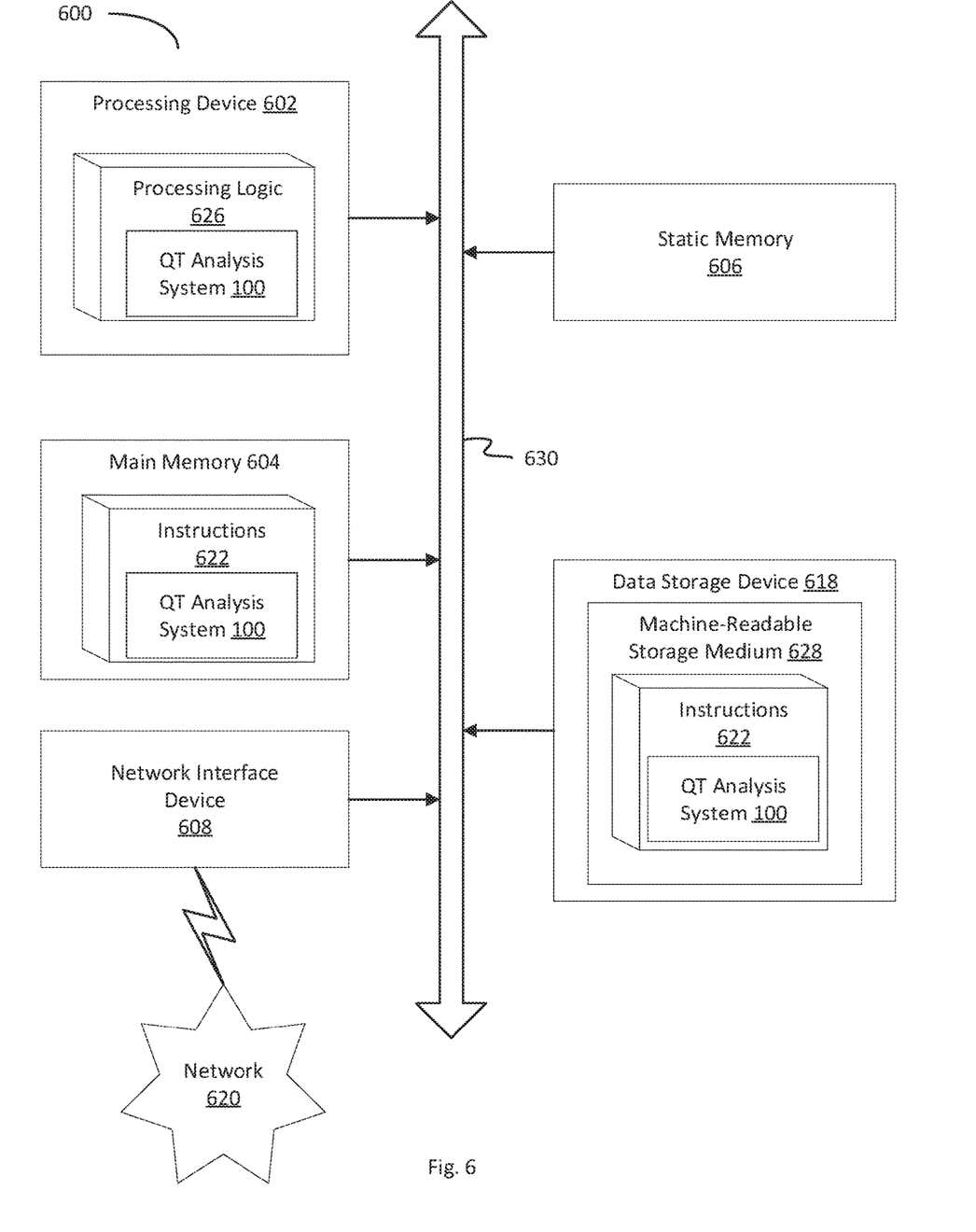
FIG. 6 illustrates an example computing environment of a QT interval measurement system, according to aspects of the disclosure.

FIG. 6 illustrates a diagrammatic representation of a machine in the example of a computer system 600 within which a set of instructions, for causing the machine to perform any one or more of the methodologies discussed herein, may be executed. In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, wearable computing device, a set-top box (STB), a Personal Digital Assistant (PDA), a cellular telephone, a web appliance, a server, a network router, a switch or bridge, a hub, an access point, a network access control device, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. In one embodiment, computer system 600 may be representative of a server, such as one or more components of QT analysis system 100 configured to perform processes as described above.

The exemplary computer system 600 includes a processing device 602, a main memory 604 (e.g., read-only memory (ROM), flash memory, dynamic random access memory (DRAM)), a static memory 606 (e.g., flash memory, static random access memory (SRAM), etc.), and a data storage device 618, which communicate with each other via a bus 630. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Processing device 602 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, or the like. The processing device 602 is configured to execute processing logic 626, which may be one example of system 400 shown in FIG. 4, for performing the operations and steps discussed herein.

The data storage device 618 may include a machine-readable storage medium 628, on which is stored one or more set of instructions 622 (e.g., software) embodying any one or more of the methodologies of functions described herein, including instructions to cause the processing device 602 to execute one or more components of QT interval measurement system 100. The instructions 622 may also reside, completely or at least partially, within the main memory 604 or within the processing device 602 during execution thereof by the computer system 600; the main memory 604 and the processing device 602 also constituting machine-readable storage media. The instructions 622 may further be transmitted or received over a network 620 via the network interface device 608.

The machine-readable storage medium 628 may also be used to store instructions to perform a method for QT interval measurement systems, as described herein. While the machine-readable storage medium 628 is shown in an exemplary embodiment to be a single medium, the term "machine-readable storage medium" should be taken to include a single medium or multiple media (e.g., a centralized or distributed database, or associated caches and servers) that store the one or more sets of instructions. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Additionally, some embodiments may be practiced in distributed computing environments where the machine-readable medium is stored on and or executed by more than one computer system. In addition, the information transferred between computer systems may either be pulled or pushed across the communication medium connecting the computer systems.

Embodiments of the claimed subject matter include, but are not limited to, various operations described herein.

These operations may be performed by hardware components, software, firmware, or a combination thereof.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

It will be appreciated that variants of the above-disclosed and other features and functions, or alternatives thereof, may be combined into may other different systems or applications. Various presently unforeseen or unanticipated alternatives, modifications, variations, or improvements therein may be subsequently made by those skilled in the art which are also intended to be encompassed by the following claims. The claims may encompass embodiments in hardware, software, or a combination thereof.

What is claimed is:

1. A method comprising:
    inputting each of a set of training electrocardiogram (EKG) measurements into a machine learning model to generate an output comprising an estimated start time of a Q-wave and an estimated end time of a T-wave for each of the set of training EKG measurements;
    comparing each of the set of outputs to a corresponding labeled start time of a Q-wave and a labeled end time of a T-wave and adjusting one or more weight matrices of the machine learning model based on the comparing to train the machine learning model;
    receiving EKG data of a subject, wherein the EKG data comprises at least a full beat of the subject; and
    inputting, by a processing device, the EKG data into the machine learning model to generate a first output comprising a segmentation of the full beat, wherein the segmentation comprises at least a start time of a Q-wave and an end time of a T-wave of the EKG data.

2. The method of claim 1, further comprising determining, by the processing device, whether a time difference between the start time of the Q-wave and the end time of the T-wave of the EKG data is greater than a threshold.

3. The method of claim 2, further comprising generating an alert indicating that the time difference satisfies the threshold in response to determining that the time difference is greater than the threshold.

4. The method of claim 2, further comprising determining a previous QT interval of the subject and generating the threshold based at least in part on the previous QT interval.

5. The method of claim 1, wherein the machine learning model comprises a neural network comprising one or more of a convolutional layer or a recurrent layer.

6. The method of claim 2, wherein the threshold is 500 milliseconds.

7. The method of claim 1, wherein inputting the EKG data into the machine learning model further generates an output identifying times associated with a P-wave, an R-wave, and an S-wave.

8. The method of claim 1, wherein the EKG data comprises a lead I measurement, a lead I and a lead II measurement, or lead I, lead II, lead III, lead aVR, lead aVL, and aVF measurements.

9. A system comprising:
    a single lead electrocardiogram (EKG) sensor; and
    a processing device communicably coupled to the single lead EKG sensor, wherein the processing device is to:
        input each of a set of training electrocardiogram (EKG) measurements into a machine learning model to generate an output comprising an estimated start time of a Q-wave and an estimated end time of a T-wave for each of the set of training EKG measurements;
        compare each of the set of outputs to a corresponding labeled start time of a Q-wave and a labeled end time of a T-wave and adjusting one or more weight matrices of the machine learning model based on the comparing to train the machine learning model;
        receive EKG data from the single lead EKG sensor;
        analyze, using the machine learning model, the EKG data to generate an output of a QT interval of the EKG data, the QT interval comprising a start time of a Q-wave and an end time of a T-wave of the EKG data;
        determine that the QT interval satisfies a threshold QT interval value; and
        generate an alert in response to determining that the QT interval satisfies the threshold value.

10. The system of claim 9, wherein inputting the EKG data into the machine learning model further generates an output identifying timing measurements associated with a P-wave, an R-wave, and an S-wave.

11. The system of claim 9, wherein
    the QT interval corresponds to a difference between the start time of the Q-wave and the end time of the T-wave of the EKG data.

12. The system of claim 9, wherein the processing device is further to determine a previous QT interval of the subject and generate the threshold based at least in part on the previous QT interval.

13. A non-transitory computer readable medium including instructions thereon that when executed by a processing device cause the processing device to:
- receive a training set of EKGs associated with a plurality of subjects, wherein each of the training set of EKGs has labeled QT interval data;
- for each EKG in the training set of EKGs:
  - input, by the processing device, the EKG into an untrained machine learning model to generate an estimated QT interval;
  - compare the estimated QT interval to the labeled QT interval data; and
  - update the untrained machine learning model based on the comparison; and
- output the untrained machine learning model as a trained machine learning model in response to determining that the untrained machine learning model has converged within a threshold level of accuracy.

14. The non-transitory computer readable medium of claim 13, wherein the labeled QT interval data comprises a first label indicating a start time of a Q-wave and a second label indicating an end time of a T-wave.

15. The non-transitory computer readable medium of claim 13, wherein to compare the estimated QT interval to the labeled QT interval data, the processing device is further to:
- compare an estimated Q-wave start time to a labeled Q-wave start time; and
- compare an estimated T-wave end time to a labeled T-wave end time.

16. The non-transitory computer readable medium of claim 13, wherein the processing device is further to:
- receive a new EKG signal from a subject;
- analyze the EKG signal to generate an output of a QT interval;
- determine that the output of the QT interval satisfies a threshold value; and
- generate an alert in response to determining that the output of the QT interval satisfies the threshold value.

17. The non-transitory computer readable medium of claim 16, wherein the EKG signal was taken from a lead I measurement.

* * * * *